United States Patent [19]
Carroll et al.

[11] Patent Number: 6,150,344
[45] Date of Patent: Nov. 21, 2000

[54] HYDROXYPHOSPHONATE PEPTIDOMIMETICS AS INHIBITORS OF ASPARTYL PROTEASES

[75] Inventors: Carolyn DiIanni Carroll, Yardley; Roland Ellwood Dolle, III, King of Prussia, both of Pa.; Yvonne Class Shimshock, Somerville; Timothee Felix Herpin, Princeton, both of N.J.

[73] Assignee: Pharmacopeia, Inc., Princeton, N.J.

[21] Appl. No.: 09/318,970

[22] Filed: May 26, 1999

Related U.S. Application Data

[62] Division of application No. 08/888,957, Jul. 7, 1997, Pat. No. 5,962,506.

[51] Int. Cl.$^7$ .......................... A61K 31/66; A61K 31/27; C07F 9/07
[52] U.S. Cl. ........................... 514/119; 514/478; 558/70; 558/170; 558/174
[58] Field of Search ........................... 558/70, 170, 174; 514/119, 478

[56] References Cited

U.S. PATENT DOCUMENTS 5,565,324  10/1996  Still et al. ..................................... 435/6

OTHER PUBLICATIONS

Rotella, D.P., "Solid Phase Synthesis of Olefin and Hydroxyethylene Peptidomimetics," *Journal of the American Chemical Society*, vol. 118, pp. 12246–12247 (1996).

Murphy, M.M. et al., "Combinatorial Organic Synthesis of Highly Functionalized Pyrrolidines . . . , " *Journal of the American Chemical Society*, vol. 117, no. 26, pp. 7029–7030 (1995).

Baldwin, J.J. et al., "Synthesis of a Small Molecule Combinatorial Library Encoded with Molecular Tags," *Journal of the American Chemical Society*, vol. 117, no. 20, pp. 5588–5599 (1995).

Wang, G.T. et al., "Synthetic Chemical Diversity: Solid Phase Synthesis of Libraries . . . ," *Journal of Medicinal Chemistry*, vol. 38, no. 16, pp. 2995–3002 (1995).

Kick, E.K. et al., "Expedient Method for the Solid–Phase Synthesis of Aspartic Acid Protease Inhibitors . . . ," *Journal of Medicinal Chemistry*, vol. 38, No. 9, pp. 1427–1430 (1995).

*Primary Examiner*—D. Margaret Seaman
*Attorney, Agent, or Firm*—Heslin & Rothenberg

[57] ABSTRACT

Compounds of Formula I

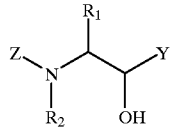

are disclosed as inhibitors having activity against the aspartyl proteases, plasmepsin and cathepsin D. The compounds are therefore useful for treatment of diseases such as malaria and Alzheimer's disease. In preferred compounds of Formula I, Y is an dialkoxyphosphonate, or α-hydroxyamide group and Z is an acyl or α-ketocarbamate functionality. Intermediates in the solid phase synthesis of compounds of Formula I, in which compounds are attached to a solid support, are also disclosed.

7 Claims, No Drawings

HYDROXYPHOSPHONATE PEPTIDOMIMETICS AS INHIBITORS OF ASPARTYL PROTEASES

CROSS REFERENCE TO RELATED APPLICATIONS

This application is a divisional of U.S. application Ser. No. 08/888,957, filed Jul. 7, 1997 now U.S. Pat. No. 5,962,506, the entire disclosure of which is incorporated herein by reference.

FIELD OF THE INVENTION

The present invention relates to analogs that display selective inhibitory activity against the aspartyl proteases, plasmepsin and cathepsin D.

BACKGROUND OF THE INVENTION

Resistance to known antimalarial therapies is becoming an increasing problem and new therapies are therefore desperately needed. Upon infecting a host, the malaria parasite avidly consumes the host hemoglobin as its source of nutrients. Plasmepsin I and II are proteases from *Plasmodium falciparum* that are necessary during the initial stages of hemoglobin hydrolysis and digestion, which occurs in the α-chain, between Phe 33 and Leu 34, then other sites serve as substrates for hydrolysis as well. In culture, inhibition of plasmepsin by a peptidomimetic inhibitor is demonstrated as effective in preventing malarial hemoglobin degradation and in killing the parasite (Francis, S. E., Gluzman, I. Y., Oksman, A., Knickerbocker, A., Mueller, R., Bryant, M. L., Sherman, D. R., Russell, D. G., and Goldberg, D. E. (1994) *EMBO J*, 13, 306–317). Thus, persons of skill in the art expect that plasmepsin inhibitors will provide effective antimalarial therapy in humans.

Cathepsin D is a human protease in the endosomal-lysosomal pathway, involved in lysosomal biogenesis and protein targeting, and may also be involved in antigen processing and presentation of peptide fragments. The protease therefore displays broad substrate specificity, but prefers hydrophobic residues on either side of the scissile bond.

Cathepsin D has been implicated in a variety of diseases, including connective tissue disease, muscular dystrophy, and breast cancer. Cathepsin D is also believed to be the protease which processes the β-amyloid precursor protein (Dreyer, R. N., Bausch, K. M., Fracasso, P., Hammond, L. J., Wunderlich, D., Wirak, D. O., Davis, G., Brini, C. M., Bucholz, T. M., Konig, G., Kamarck, M. E., and Tamburini; P. P. (1994) *Eur. J. Biochem.*, 224, 265–271 and Ladror, U. S., Synder, S. W., Wang, G. T., Holzman, T. F., and Krafft, G. A. (1994) *J. Biol. Chem.*, 269, 18422–18428), generating the major component of plaques in the brains of Alzheimer's patients. Consequently, persons of skill in the art expect that inhibitors of cathepsin D will be useful in treating Alzheimer's disease.

The present invention relates to peptidomimetic (hydroxystatine amides and hydroxyphosphonates) analogs and their inhibitory action against aspartyl proteases. More particularly, the invention relates to the identification of such compounds that display selective inhibitory activity against plasmepsin and cathepsin D. Although statine-containing peptides are known which inhibit aspartyl proteases (Shewale, J. G.; Takahashi, R.; Tang, J., Aspartic Proteinases and Their Inhibitors, Kostka, V., Ed. Walter de Gruyter: Berlin (1986) pp. 101–116; U.S. Ser. No. 08/743,944, filed Nov. 5, 1996, which is hereby incorporated by reference in its entirety), there are only a few selective inhibitors for cathepsin D (Lin, T.-Y.; Williams, H. R., Inhibition of Cathepsin D by Synthetic Oligopeptides, *J. Biol. Chem.* (1979), 254, 11875–11883; Rich, D. H.; Agarwal, N. S., Inhibition of Cathepsin D by Substrate Analogues Containing Statine and by Analogues of Pepstatin, *J. Med. Chem.* (1986) 29 (2519–2524)), and for plasmepsin (Silva, A. M. et al., Structure and Inhibition of Plasmepsin II, A Hemoglobin-Degrading Enzyme From *Plasmodium falciparum, Proceed Natl Acad Sci,* 1996, 93, 10034–10039).

The present invention also relates to the solid phase synthesis of such peptidomimetic analogs.

SUMMARY OF THE INVENTION

I. Preferred Embodiments

The compounds of the present invention are represented by Formula I:

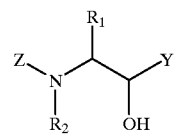

I wherein:

$R^1$ is chosen from the group consisting of alkyl, —$(CH_2)_n$-cycloalkyl, —$(CH_2CH_2)_n$NHC(O)-alkyl, and arylalkyl, wherein n=1–3;

$R^2$ is H or ⓢ—C(O)—L—, wherein ⓢ is a solid support, and —L— is a linker;

Y is —P(O)(OR$^3$)$_2$ or —CH(OH)C(O)NR$^4$R$^5$, wherein $R^3$ is alkyl, arylalkyl, or haloalkyl; and $R^4$ and $R^5$ are independently chosen from the group consisting of H, alkyl —$(CH_2)_n$-cycloalkyl, —$(CH_2CH_2)_n$NHC(O)-alkyl, arylalkyl,

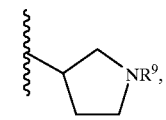

—C(H)(R$^9$)CH$_2$OR$^{10}$, —C(H)(R$^{11}$)C(H)(OR$^{10}$)(R$^{11}$), -alkyl-NHSO$_2$R$^{11}$, —C(H)(R$^9$)C(O)NHR$^{10}$, and —C(H)(R$^9$)C(O)NHC(H)(R$^9$)C(O)NHR$^{10}$, wherein n=1–3;

$R^9$ is independently selected from the group consisting of alkyl and arylalkyl;

$R^{10}$ is independently selected from the group consisting of H, alkyl, and arylalkyl;

$R^{11}$ is independently selected from the group consisting of alkyl and aryl; or, when taken together, $R^4$ and $R^5$ can be

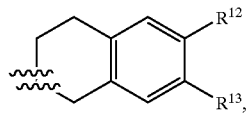

wherein
R$^{12}$ and R$^{13}$ are independently selected from the group consisting of H, halo, and alkoxy; and
Z is —C(O)R$^6$ and —C(O)C(H)(R$^7$)OC(O)NHR$^8$, wherein R$^6$ is alkyl, arylalkyl, aryl, —(CH$_2$)$_m$-cycloalkyl, heteroaryl, or

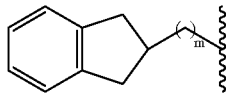

wherein m=0–3;
R$^7$ is H, alkyl, arylalkyl, or —(CH$_2$)$_n$-cycloalkyl; and
R$^8$ is alkyl, arylalkyl, or aryl.
Preferred compounds of Formula I are those wherein —L— is of Formula (a)

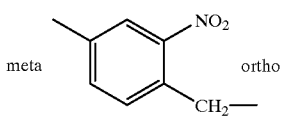

wherein the designated meta-position is attached to the —C(O)— and the ortho-methylene attaches to the amide nitrogen of Formula I.

A preferred embodiment of the invention are compounds of Formula I wherein:
Y is —P(O)(OR$^3$)$_2$, wherein R$^3$ is arylalkyl; and

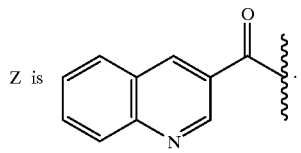

Another preferred embodiment of the invention are compounds of Formula I wherein:
Y is —C(H)(OH)C(O)NHR$^5$, wherein R$^5$ is

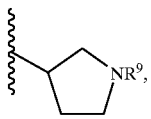

wherein R$^9$ is independently selected from the group consisting of alkyl and arylalkyl; and

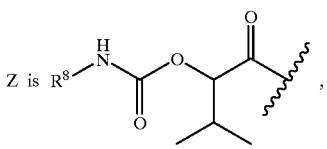

wherein R$^8$ is alkyl or arylalkyl.

A further preferred embodiment of the invention are compounds of Formula I wherein:
Y is —C(H)(OH)C(O)NHR$^5$, wherein R$^5$ is —C(H)(R$^{11}$)C(H)(OR$^{10}$)(R$^{11}$), wherein R$^{11}$ is aryl and R$^{10}$ is H, wherein each R$^{11}$ may be the same or different; and

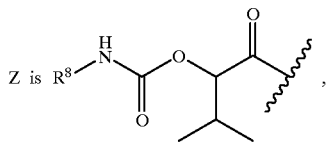

wherein R$^8$ is alkyl or arylalkyl.

Yet another preferred embodiment of the invention are compounds of Formula I wherein:
Y is —C(H)(OH)C(O)NHR$^5$, wherein R$^5$ is —C(H)(R$^{11}$)C(H)(OR$^{10}$)(R$^{11}$), wherein R$^{11}$ is aryl and R$^{10}$ is H, wherein each R$^{11}$ may be the same or different; and
Z is R$^6$C(O)—, wherein R$^6$ is alkyl, arylalkyl, —(CH$_2$)$_m$-cycloalkyl, or

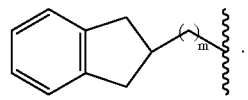

Another aspect of the invention is the use of divinylbenzene-cross-linked, polyethyleneglycol-grafted polystyrene beads optionally functionalized with amino groups (e.g., TentaGel™ S NH$_2$, Rapp Polymere) as the solid supports for constructing compounds of Formula I.

DETAILED DESCRIPTION OF THE INVENTION

II. Abbreviations and Definitions

The following abbreviations and terms have the indicated meanings throughout:

| | |
|---|---|
| Ac | = Acetyl |
| BNB | = 4-bromomethyl-3-nitrobenzoic acid |
| BOC | = t-butyloxycarbonyl |
| BSA | = bovine serum albumin |
| Bu | = butyl |
| c- | = cyclo |
| DABCYL | = 4-(4-dimethylaminophenylazo)benzoic acid |
| DBU | = Diazabicyclo[5.4.0]undec-7-ene |
| DCM | = Dichloromethane = methylene chloride = CH$_2$Cl$_2$ |
| DIC | = diisopropylcarbodiimide |
| DIEA | = diisopropylethyl amine |
| DMAP | = 4-N,N-dimethylaminopyridine |
| DMF | = N,N-dimethylformamide |
| DMSO | = Dimethyl sulfoxide |
| DVB | = 1,4-divinylbenzene |
| EDANS | = 5-[(2-aminoethyl)amino]naphthalene-1-sulfonic acid |
| Et | = ethyl |
| Fmoc | = 9-fluorenylmethoxycarbonyl |
| HOAc | = acetic acid |
| HOBt | = hydroxybenzotriazole |
| IBX | = iodoxybenzoic acid |
| LiI | = lithium iodide |
| m- | = meta |
| Me | = methyl |
| NMO | = N-methylmorpholine oxide |
| o- | = ortho |
| PEG | = polyethylene glycol |
| Ph | = phenyl |
| PfP | = pentafluorophenol |
| r.t. | = room temperature |
| sat'd | = saturated |
| s- | = secondary |
| t- | = tertiary |
| TBS | = tert-butyldimethylsilyl |
| TFA | = trifluoroacetic acid |
| THF | = tetrahydrofuran |

-continued

TMS = trimethylsilyl
Tris = tris(hydroxymethyl)aminomethane
UV = ultraviolet light "Alkoxy" means alkoxy groups of from 1 to 8 carbon atoms of a straight, branched, or cyclic configuration and combinations thereof. Examples of alkoxy groups include methoxy, ethoxy, propoxy, isopropoxy, cyclopropyloxy, cyclohexyloxy, and the like.

"Alkyl" is intended to include linear or branched hydrocarbon structures and combinations thereof. "Lower alkyl" means alkyl groups of from 1 to 12 carbon atoms. Examples of alkyl groups include methyl, ethyl, propyl, isopropyl, butyl, s-and t-butyl, pentyl, hexyl, octyl, and the like.

"Aryl" is a 6-membered or 10-membered aromatic ring system where each of the rings is optionally substituted with 1–3 substituents selected from alkyl, halogen, hydroxy, alkoxy, aryloxy, alkoxyethoxy, haloalkyl, phenyl, heteroaryl; and wherein the phenyl is optionally substituted with 1–3 substituents selected from alkyl, halogen or alkoxy. Examples of aryl groups are phenyl, 3,4-dimethoxyphenyl and naphthyl.

"Arylalkyl" means an alkyl containing an aryl ring. For example: benzyl, phenethyl, 4-chlorobenzyl, and the like.

"Aryloxy" means a phenoxy group where the phenyl ring is optionally substituted with 1 to 2 groups selected from halo, alkoxy, or alkyl.

"Cycloalkyl" includes cyclic hydrocarbon groups of from 3 to 12 carbon atoms. Examples of "cycloalkyl" groups include c-propyl, c-butyl, c-pentyl, c-hexyl, 2-methylcyclopropyl, norbornyl, adamantyl, and the like.

"Haloalkyl" means that one or more hydrogen atoms present in an alkyl group are substituted with a halogen atom, except for the methylene hydrogens adjacent to the oxygen atom. For example: 2-chloroethyl, and 2,2,2-trifluoroethyl.

"Halogen" includes F, Cl, Br, and I, with F and Cl as the preferred groups.

"Heteroaryl" means a 5- or 6-membered heteroaromatic ring containing 0–2 heteroatoms selected from O, N, and S; or a bicyclic 9- or 10-membered heteroaromatic ring system containing 0–2 heteroatoms selected from O, N, and S; where the methine H atom may be optionally substituted with alkyl, alkoxy or halogen. The 5- to 10-membered aromatic heterocyclic rings include imidazole, pyridine, indole, thiophene, benzopyranone, thiazole, furan, benzimidazole, quinoline, isoquinoline, quinoxaline, pyrimidine, pyrazine, tetrazole, and pyrazole.

"Heteroarylalkyl" means an alkyl containing a heteroaryl ring. For example: pyridinylmethyl, pyrimidinylethyl, and the like.

The material upon which the syntheses of the invention are performed are referred to as solid supports, beads, and resins. These terms are intended to include: beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and soluble supports such as low molecular weight non-cross-linked polystyrene.

III. Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R)- or (S)-, or as (D)- or (L)- for amino acids. The present invention is meant to include all such possible diastereomers as well as their racemic and optically pure forms. Optically active (R)- and (S)-, or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended to include both (E)- and (Z)- geometric isomers. Likewise, all tautomeric forms are intended to be included.

IV. Assays for Determining Biological Activity

Materials

Plasmepsin II was obtained from Daniel E. Goldberg, Washington University. The plasmepsin II substrate, (DABCYL)-γ-aminobutyric acid-Glu-Arg-Met-Phe-Leu-Ser-Phe-Pro-EDANS, and the cathepsin D substrate, DABCYL-γ-aminobutyric acid-Lys-Pro-Ile-Glu-Phe-Phe-Arg-Leu-EDANS or Ac-Glu-Glu(EDANS)-Lys-Pro-Ile-Met-Phe-Phe-Arg-Leu-Gly-Lys-(DABCYL)-Glu-NH$_2$ (Sergei V. Gulnik and John W. Erickson, National Cancer Institute) were purchased as a custom synthesis from AnaSpec, Inc., 2149 O'Toole Avenue, Suite F, San Jose, Calif. 95131.

Cathepsin D from human liver was purchased from ART Biochemicals, Athens Research Technology, PO Box 5494, Athens, Ga. 30604.

Method for Plasmepsin II

The assay mix contained 50 mM sodium acetate (pH 5.0), 1 mg/ml BSA, 0.01% Tween 20, 12.5% glycerol, 18% DMSO and 12 µM plasmepsin substrate. Twenty five µL of the assay mix was added to each well of the 96-well microtiter plate containing dried down bead eluate or empty control wells. The plates were then sonicated and mixed. Twenty five µL of 8 nM plasmepsin II in 50 mM sodium acetate (pH 5.0), 1 mg/ml BSA, 0.01% Tween 20, and 12.5% glycerol, were added to the assay mix. The final concentrations were 4 nM plasmepsin II, 6 µM plasmepsin substrate, 9% DMSO, 50 mM sodium acetate (pH 5.0), 1 mg/ml BSA, 0.01% Tween 20, and 12.5% glycerol. The reaction was incubated for 10 minutes at 25° C. and then quenched by the addition of 25 µL of 1 M Tris (pH 8.5) and 50% DMSO to achieve a final concentration of 0.33 M Tris and 23% DMSO. The EDANS fluorescence was measured using the Tecan, SLT FluoStar fluorescence plate reader with an excitation filter of 350 nm and an emission filter of 510 nm. The background was determined by 25 µL of 50 mM sodium acetate (pH 5.0), 1 mg/ml BSA, 0.01% Tween 20, and 12.5% glycerol without enzyme.

Method for Cathepsin D

The assay mix contained 25 mM sodium formate (pH 3.5), 1 mg/ml BSA, 12% DMSO and 12 µM cathepsin D substrate. Twenty five µL of the assay mix were added to each well of the 96-well microtiter plate containing dried down bead eluate or empty control wells. The plates were then sonicated and mixed. Twenty five µL of 1.6 nM cathepsin D in 25 mM sodium formate (pH 3.5), and 1 mg/ml BSA, were added to the assay mix. The final concentrations were 0.8 nM cathepsin D, 6 µM cathepsin D substrate, 6% DMSO, 25 mM sodium formate (pH 3.5), and 1 mg/ml BSA. The reaction was incubated for 10 minutes at 25° C. and then quenched by the addition of 25 µL of 1 M Tris (pH 8.5) and 50% DMSO to achieve a final concentration of 0.33 M Tris and 21% DMSO. The EDANS fluorescence was measured as stated above. The background was determined by 25 μL of 50 mM sodium formate (pH 3.5), and 1 mg/ml BSA without enzyme.

V. Methods of Synthesis

The compounds of the present invention may be prepared according to the following methods. In carrying out the syntheses, one typically begins with a quantity of solid support that will provide enough compound after cleavage from the solid support for biological testing in the herein described assays. In the case where the solid support is TentaGel™, it is recommended that approximately 0.5 g of beads of about 180 microns in diameter, with a loading capacity of about 300 picoM per bead, be used. As the chemical yield of compounds after photolysis typically ranges from approximately 20% up to 60%, this quantity will provide a yield (approximately >10 mg) sufficient for biological testing in the given protease assays. For actual synthesis, the appropriate reagents and reaction conditions are applied to a reaction vessel containing the specified quantity of beads. During the syntheses, the beads may be washed free of any excess reagents or by-products before proceeding to the next reaction.

A. Scheme 1: Synthesis of Hydroxyphosphonates

A batch of amino-functionalized PEG-grafted polystyrene beads such as TentaGel™ 1 is used in the synthesis. The batch was first treated with bis-Fmoc lysine to increase the loading capacity of the resin. The Fmoc groups were removed using piperidine under standard conditions to which was then added 4-bromomethyl-3-nitrobenzoic acid 2. This was accomplished by the following method. The amine resin was suspended in DMF, and treated with a solution of 2, HOBt, DIC in DMF. The suspension was shaken overnight, then drained and the resin was washed with DCM. The resin 3 was dried overnight in vacuum.

Resin 3 was reacted with a unique amino-TBS ether to generate resin 4. The coupling of each amine occurred through displacement of the linker bromide and formation of a new carbon-nitrogen bond. Two cycles of reactions were performed to ensure complete conversion. In the first cycle, the amine was added to a suspension of resin 3 in THF and the mixture was shaken overnight. The mixture was drained and the resin was washed with THF. The THF solution containing the excess amine was then concentrated, taken up in DCM, washed with aqueous sodium bicarbonate, dried over sodium sulfate and concentrated. The residue was taken up in DMF and reacted with the same resin for the second reaction cycle. Lithium iodide was added to the suspension and the mixture was shaken overnight. The suspension was drained and the resin was washed with DMF, methanol, DCM and dried overnight in vacuum to give resin 4. After coupling, a small portion of each batch of resin was removed and titrated with picric acid to determine the extent of amine loading as a quality control for the reaction in this step.

The amine 4 was acylated by using acid chlorides. An acid chloride was added to a suspension of amine resin 4 in pyridine. The mixture was shaken overnight, drained and the resin was washed with DMF, methanol and DCM. When using acid chloride 6, the chloromethylacetoxy group was removed with hydrazine in methanol for 1 hour at r.t., drained, washed with DCM and acetonitrile. The resin 8 so obtained was shaken with an isocyanate in acetonitrile in the presence of a base overnight. The resin was finally drained and washed with DMF, methanol, DCM. This gave the carbamate derivatized resin 9.

Either resin 5 or 9 was converted to the corresponding aldehyde resin 10 by deprotection and oxidation. Resin 5 or 9 was treated with dilute hydrochloric acid in methanol for 5–8 hr to remove the t-butyldimethylsilyl (TBS) protecting group. The resin was then washed with DMF, methanol and DCM. The resulting alcohols were oxidized to the corresponding aldehydes by the following method: To a suspension of the resin in DMSO was added a solution of IBX in DMSO and the mixture was shaken overnight. The suspension was drained and the resin was washed with DMSO and treated with another solution of IBX in DMSO for 4 hr. The mixture was then drained and the resin washed with DMSO, methanol, DCM and dried overnight in vacuum to give the aldehydes 10.

To a suspension of the resin 10 in DCM was added a phosphite followed by triethylamine and the mixture was shaken overnight. The suspension was drained and the resin 11 was washed with DMF, methanol, DCM. Amides of Formula I (i.e., compounds 12) were cleaved from resin compounds 11 by exposing them to UV light (ca. 360 nM) for 15–180 minutes at 25–50° C. in a suitable solvent such as methanol.

B. Scheme 2: Synthesis of Hydroxystatine amides

In this chemistry, the resin bound aldehyde 10 (from Scheme 1) was converted to the diacetate ester 15 by a Wittig reaction, followed by catalytic dihydroxylation of the alkene and protection of the diol as a diacetate. The resin bound aldehydes 10 suspended in THF were reacted with (t-butoxycarbonylmethylene)-triphenylphosphorane overnight. After washing with THF, methanol and DCM, the α,β-unsaturated esters 13 were suspended in acetone-water (1:1 mixture) and NMO was added along with a solution of osmium tetroxide in water. The mixture was shaken overnight, drained and the resin was washed with water, pyridine, DMF, methanol and DCM. Protection of the diol 14 was accomplished by treatment of the resin with a solution of acetic anhydride in pyridine containing a catalytic amount of DMAP for 18 hr. The resin was subsequently washed with DMF, methanol and DCM and dried overnight in vacuum to give the diacetate resin 15.

The ester-diacetate 15 was converted to the corresponding acid, which was then coupled with an amine. Deprotection of the diacetate amide resin 19 then led to the resin 20. Hydrolysis of ester 15 was accomplished by treatment with neat TFA for 2 hr. The resin was then washed with DMF, methanol and DCM, and suspended in a small amount of a 1:1 mixture of DMF:pyridine. Pentafluorophenyl trifluoroacetate was added along with pentafluorophenol and the mixture was shaken 1 hr at r.t., then drained. The resin bound activated ester 18 was washed briefly with DMF and treated overnight with a DMF solution of an amine. After washing with DMF, methanol and DCM, the amide-diacetate 19 was shaken 2 hr in a solution of hydrazine in methanol to afford resin bound diol 20. The resin bound diol 20 was washed with DMF, methanol and DCM and dried overnight in vacuum. Amides of Formula I (i.e., compounds 21) may be cleaved from resin compounds 20 by exposing them to UV light (ca. 360 nM) for 15–180 minutes at 25–50° C. in a suitable solvent such as methanol.

EXAMPLE 1

ENTRY 9, TABLE 1

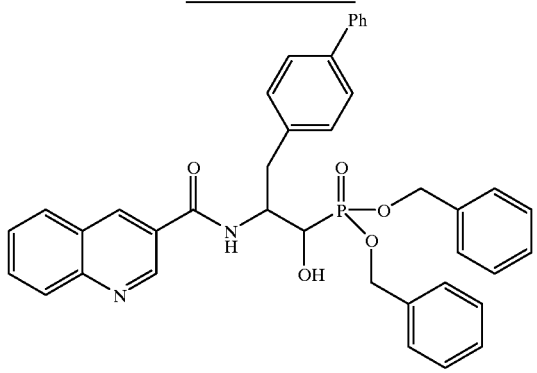

TentaGel™ resin (S-NH$_2$, 1.2 g, 0.032 mmol/g, 0.384 mmol, 180–220 μm) was suspended in a solution of bis-Fmoc lysine (1.12 mmol, 0.68 g), and HOBt (1.12 mmol, 0.15 g), then treated with DIC (2.2 mmol, 0.36 mL). The suspension was shaken overnight, then drained and washed with DMF (3×15 mL), MeOH (3×15 mL), and CH$_2$Cl$_2$ (3×15 mL).

A suspension of the Fmoc resin (1.2 g) in 1:1 piperidine-DMF was shaken 1.5 hr, then drained and washed with DMF (3×12 mL), MeOH (3×12 mL), and CH$_2$Cl$_2$ (3×12 mL). This resin was suspended in DMF (4 mL), and treated with a pre-incubated (1 hr) solution of 4-bromomethyl-3-nitro benzoic acid (2.2 mmol, 0.58 g), HOBt (2.3 mmol, 0.3 g), and DIC (4.5 mmol, 1 mL) in DMF (6 mL). The suspension as shaken overnight, then drained and washed with DMF (3×12 mL), methanol 3×12 mL), and DCM (3×12 mL).

The suspension of the resin (1.2 g) in THF (30 mL) was treated with t-butyldimethylsilyl-4-(phenyl)phenylalaninol (1 mmol), and shaken overnight. The resin was then drained and washed with THF (2×20 mL). The filtrate was concentrated and the residue was taken up in DCM (20 mL), then washed with saturated aqueous sodium bicarbonate (20 mL). The aqueous phase was extracted with DCM (20 mL) and the combined organic phase was dried over sodium sulfate and concentrated under vacuum. The residue was then added to a suspension of the same resin in DMF (10 mL) along with lithium iodide (0.7 mmol, 0.1 g). The mixture was shaken for 24 hr and drained. The resin was washed with DMF (20 mL), MeOH (32 mL), and CH$_2$Cl$_2$ (3×20 mL). The resin 4 was collected by filtration and dried overnight in vacuum.

The suspension of resin 4 (1.67 g) in pyridine (10 mL) was treated with a 3-quinoline carboxylic acid chloride (14.8 mmol). This suspension was shaken overnight, then drained and washed with DMF (3×10 mL), MeOH (3×10 mL), DMF (3×10 mL), and CH$_2$Cl$_2$ (3×10 mL).

The resin (1 g) was suspended in a 1% solution (by volume) of concentrated HCl in methanol (15 mL). The mixture was shaken for 7 hr, drained and the resin was washed with methanol (1×15 mL), DMF (3×15 mL), methanol (3×15 mL), and DCM (3×15 mL).

The resin (1 g) was suspended in DMSO (13 mL) and a solution of IBX in DMSO (2.2 mmol, 2 mL of a 0.031 g/mL solution) was added. The mixture was shaken overnight, drained and the resin was washed with DMSO (13 mL). The resin (1 g) was suspended in DMSO again and another solution of IBX (2.2 mmol, 2 mL of a 0.031 g/mL solution) was added. The mixture was shaken for 4 hr and drained. The resin was washed with DMSO (3×15 mL), methanol (3×15 mL), and DCM (3×15 mL). The resin was collected by filtration and dried overnight in vacuum to provide resin 10.

A phosphite (9.2 mmol) ) was added to the resin 10 (1 g) suspended in DCM (30 mL) followed by triethylamine (9.2 mmol). The mixture was shaken for 18 hr, then drained. The resin was washed with DMF (3×30 mL), methanol (3×30 mL), and DCM (3×30 mL) and dried overnight in vacuum to give resin 11.

The resin was suspended in MeOH (20 mL) and the compound cleaved from the resin by heating the suspension to 50° C. and irradiating for 3–4 hr at 353 nm. The suspension was filtered, and the MeOH removed to give the title compound as confirmed by mass spectroscopy (mass spectrum: m/z=643 (M+H$^+$)).

EXAMPLE 2

ENTRY 3, TABLE 1

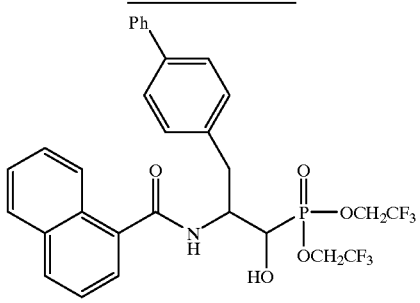

The reaction conditions used to prepare the inhibitor of Example 1 were employed to prepare Example 2. 4-(Phenyl) phenylalaninol, 1-naphthylcarboxylic acid and di(2,2,2-trifluoromethoxy)phosphite were used as starting materials. The title compound was obtained and mass spectroscopic data confirmed the molecular weight (mass spectrum: m/z= 626 (M+H$^+$)).

EXAMPLE 3

ENTRY 5, TABLE 2

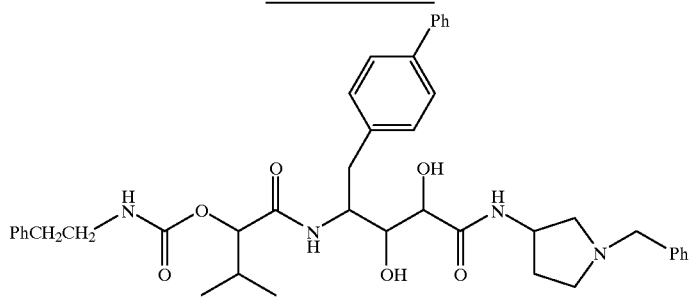

Resin 4 (obtained from Example 1; 1.67g) was suspended in pyridine (10 mL) and treated with acid chloride 6 (7.4 mmol, 1.3 mL). The suspension was shaken for 1.5 hr, drained and washed with DMF (3×10 mL), methanol (3×10 mL) and DCM (3×10 mL). The resin 7 (1.67g) was shaken 1 hr in a 10% hydrazine-methanol (4×10 mL) solution, then drained and washed with DMF (3×10 mL), methanol (3×10 mL) and DCM (3×10 mL). To the suspension of the resin (1.67 g) in acetonitrile (10 mL) was added phenethylisocyanate (14.8 mmol) along with a catalytic amount of DBU. The mixture was shaken overnight, drained, and the resin was washed with DMF (3×10 mL), methanol (3×10 mL) and DCM (3×10 mL), providing resin 9.

The resin 9 (1 g) was suspended in a 1% solution (by volume) of concentrated HCl in methanol (15 mL). The mixture was shaken for 7 hr, drained and the resin was washed with methanol (1×15 mL), DMF (3×15 mL), methanol (3×15 mL), and DCM (3×15 mL).

The resin (1 g) was suspended in DMSO (13 mL), and a solution of IBX in DMSO (2.2 mmol, 2 mL of a 0.031 g/mL solution) was added. The mixture was shaken overnight, drained, and the resin was washed with DMSO (13 mL). The resin (1 g) was suspended in DMSO and another solution of IBX (2.2 mmol, 2 mL of a 0.031 g/mL solution) was added. The mixture was shaken for 4 hr, drained, and the resin was washed with DMSO (3×15 mL), methanol (3×15 mL), and DCM (3×15 mL). The resin was dried overnight in vacuum to provide resin 10.

The resin aldehyde 10 (1 g) was suspended in THF, and (t-butoxycarbonylmethylene)-triphenylphosphorane (2.3 mmol, 0.84 g) was added. The mixture was shaken overnight, drained, and the resin was washed with THF (3×15 mL), methanol (3×15 mL) and DCM (3×15 mL) to give resin 13.

The resin 13 (1 g) was then suspended in a 1:1 mixture of acetone-water (15 mL), and NMO (2 mmol, 0.21 g) was added along with a solution of osmium tetroxide in water (0.09 mmol, 1 mL of a 4% (weight) solution). The mixture was shaken overnight, drained, and the resin was washed with water (3×15 mL), pyridine (3×15 mL), DMF (3×15 mL), methanol (3×15 mL), and DCM (3×15 mL) to give resin 14.

The resin 14 (1 g) was subsequently suspended in pyridine (9 mL), and acetic anhydride (6 mL) was added along with a catalytic amount of DMAP. The mixture was shaken overnight, drained, and washed with DMF (3×15 mL), methanol (3×15 mL), DCM (3×15 mL), then dried 5 hr in vacuum to give resin 15.

The resin 15 (1 g) was suspended in TFA, shaken for 2 hr and the mixture was drained. The resin 16 was washed with DMF (3×20 mL), methanol (3×20 mL), and DCM (3×20 mL). To the resin (1 g) suspended in DMF (2 mL) was added pyridine (2 mL), pentafluorophenol (1 g) and pentafluorophenyl trifluoroacetate 17 (2 mL). The mixture was shaken 1 hr, then drained and the resin 18 was rinsed with DMF (2×20 mL). The resin 18 (1 g) was suspended in DMF (2 mL) and N-benzyl aminopyrrolidine (10 equivalents) was added. The mixture was shaken overnight, drained, and the resin was washed with DMF (3×20 mL), methanol (3×20 mL) and DCM (3×20 mL) to give resin 19. The resin 19 was then suspended in a 10% solution of hydrazine in methanol (20 mL), shaken for 2 hr, drained, and washed with methanol (20 mL), DMF (3×20 mL), methanol (3×20 mL), and DCM (3×20 mL) to afford resin 20.

The resin was suspended in MeOH (20 mL) and the compound cleaved from the resin by heating the suspension to 50° C. and irradiating for 3–4 hr at 353 nm. The suspension was filtered and the MeOH removed to give the title compound as confirmed by mass spectroscopy (mass spectrum: m/z=708 (M+H$^+$)).

EXAMPLE 4

ENTRY 18, TABLE 2

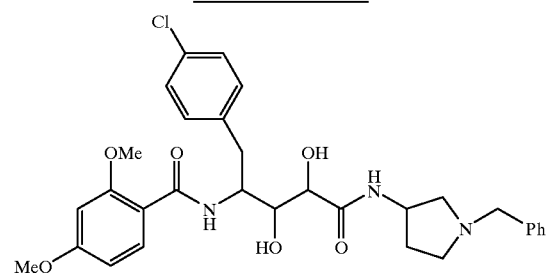

The reaction conditions used to prepare the inhibitor of Example 3 were employed to prepare Example 4. Chlorophenylalaninol, 2,4-dimethoxybenzoic acid and N-benzyl aminopyrrolidine were used as starting materials. The title compound was obtained and mass spectroscopic data confirmed the molecular weight (mass spectrum: m/z= 583 (M=H$^+$)).

Using these methods, compounds in Tables 1 and 2 were prepared. The compounds in Tables 1 and 2 typically show some measure of selectivity for either plasmepsin or cathepsin D at an inhibitory concentration ($IC_{50}$) less than 50 micromolar.
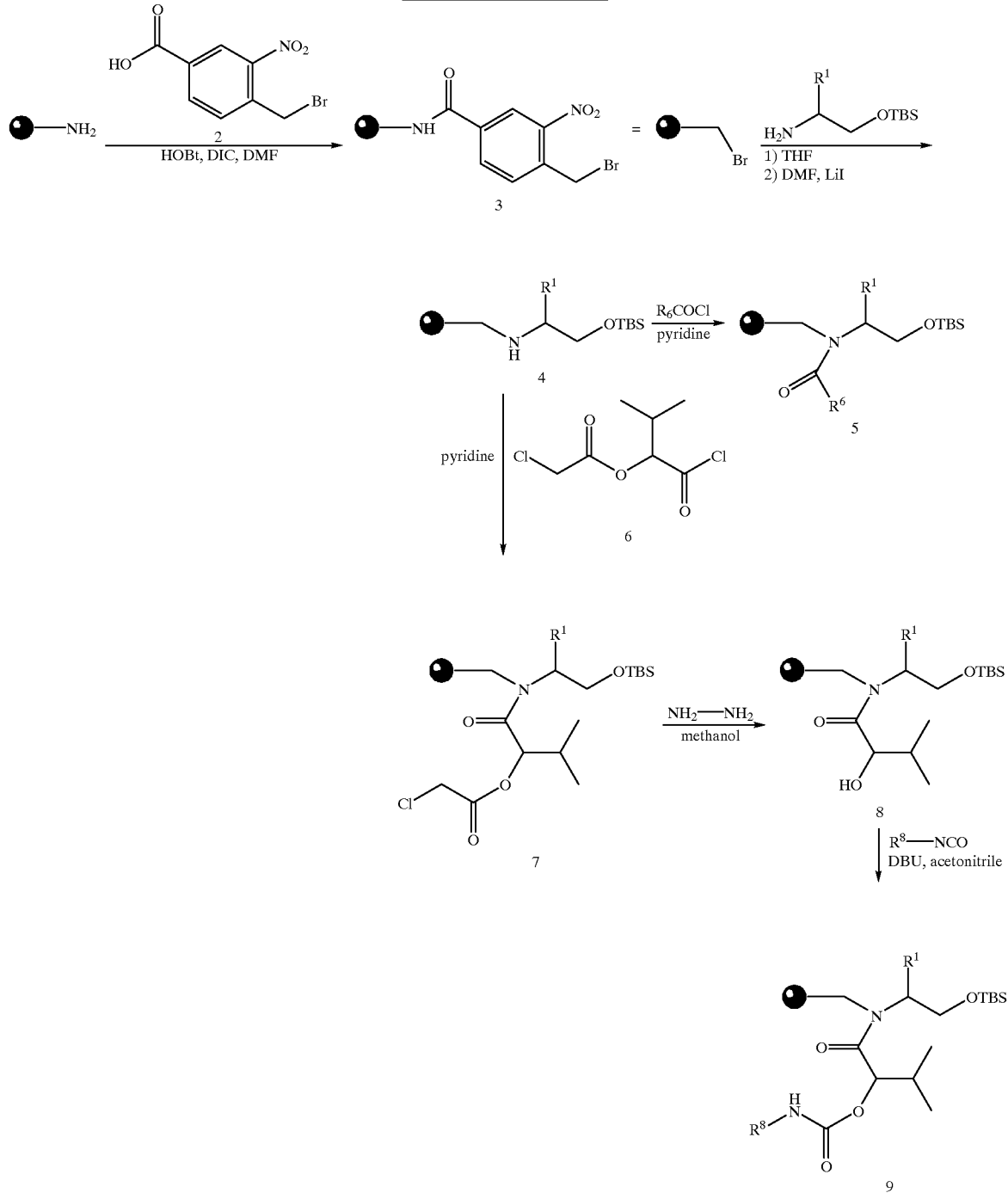

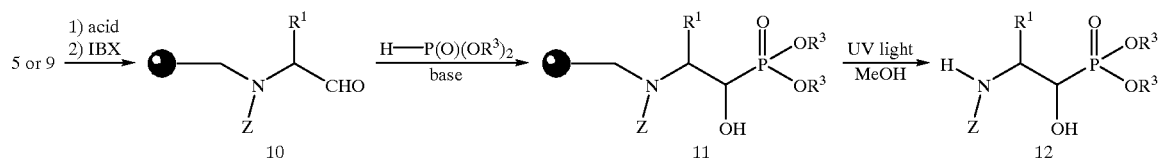
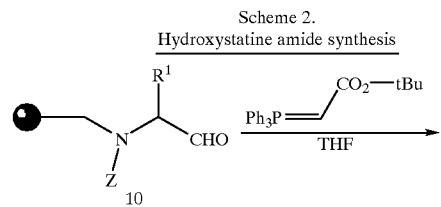
Scheme 2.
Hydroxystatine amide synthesis
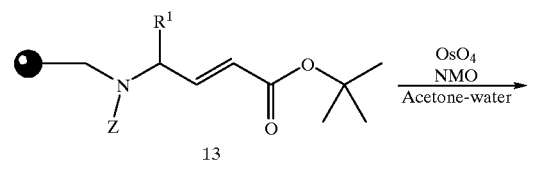
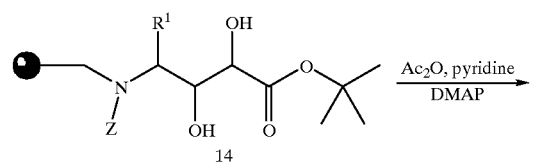
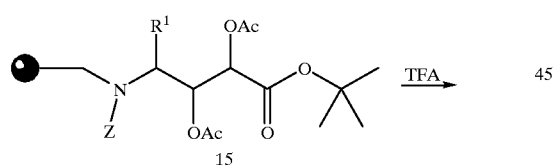
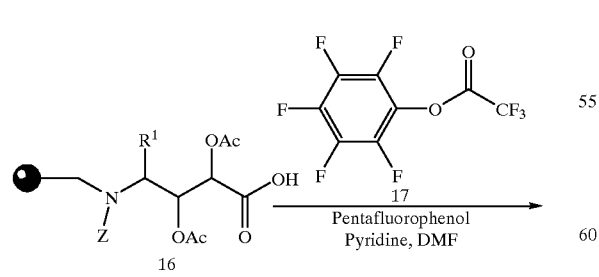
-continued
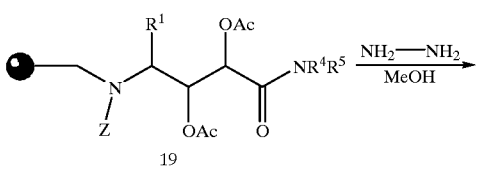
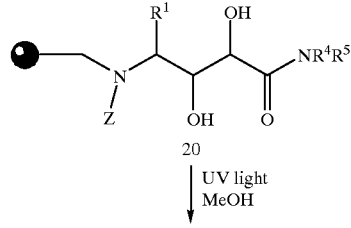
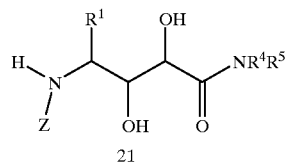

TABLE 1

Hydroxyphosphonates - Plasmepsin Inhibitors

| Entry | Structure |
|---|---|
| 1 | 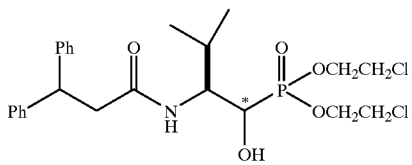 |
| 2: R = OMe  3: R = Ph | |
| 4 | 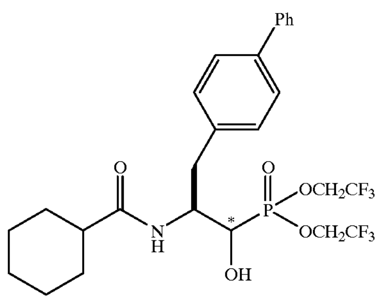 |
| 5 | 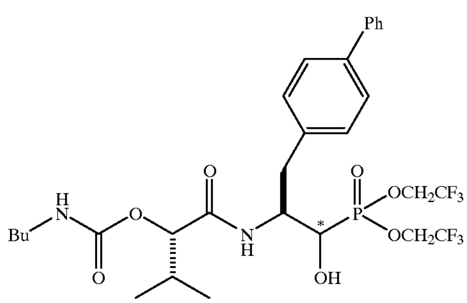 |
| 6 | 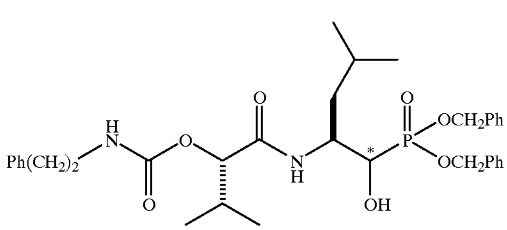 |

TABLE 1-continued

Hydroxyphosphonates - Plasmepsin Inhibitors

| Entry | Structure |
|---|---|
| 7: R = H  8: R = Cl | (3,4-dimethoxyphenyl)propanoyl-NH-CH(CH2-C6H3(Cl)(R))-CH(OH)-P(=O)(OCH2Ph)2 |
| 9: R = Ph  10: R = Cl | quinoline-3-carbonyl-NH-CH(CH2-C6H4-R)-CH(OH)-P(=O)(OCH2Ph)2 |
| 11 | quinoline-3-carbonyl-NH-CH(CH2-C6H3(3,4-Cl2))-CH(OH)-P(=O)(OCH2Ph)2 |

* denotes R or S stereochemistry

TABLE 2

Hydroxystatines amides - Plasmepsin Inhibitors

| Entry | Structure |
|---|---|
| 1 | Ph(CH2)2-NH-C(=O)-O-CH(iPr)-C(=O)-NH-CH(CH2-C6H4-Cl)-CH(OH)-CH(OH)-C(=O)-NH-CH(CH3)-C(=O)-NHBu |

TABLE 2-continued
2 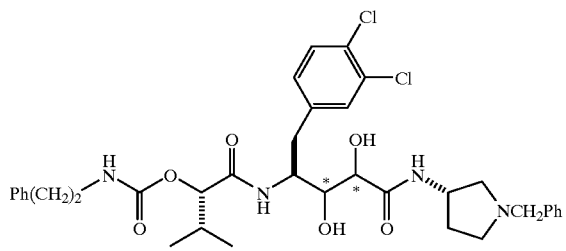
3 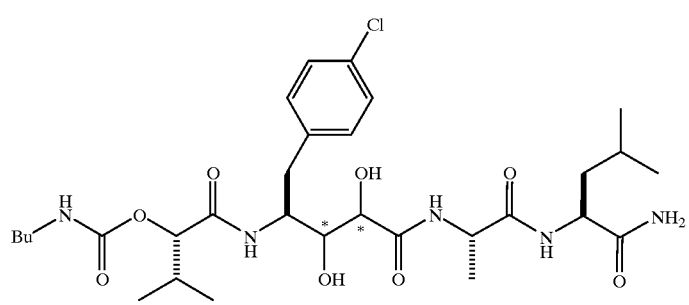
4 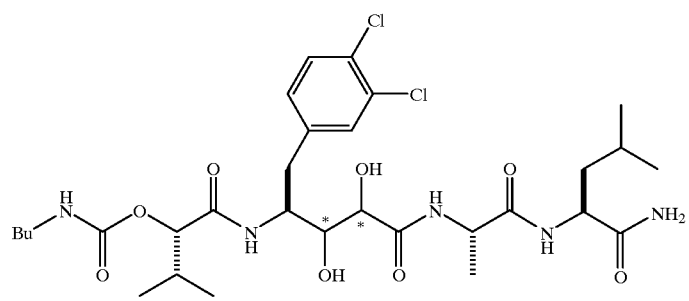
5 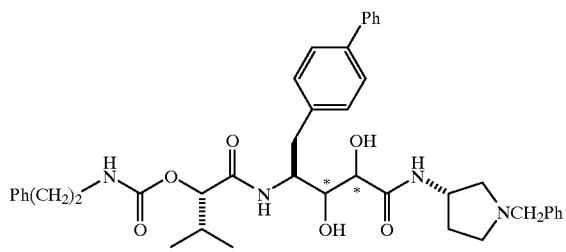
6 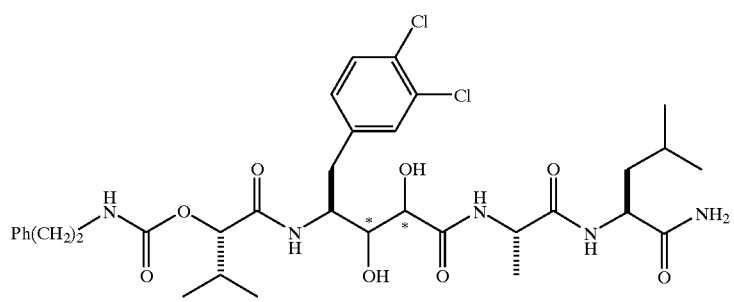

TABLE 2-continued
7 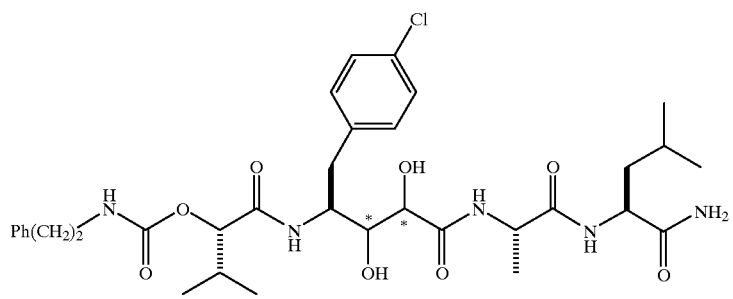
8 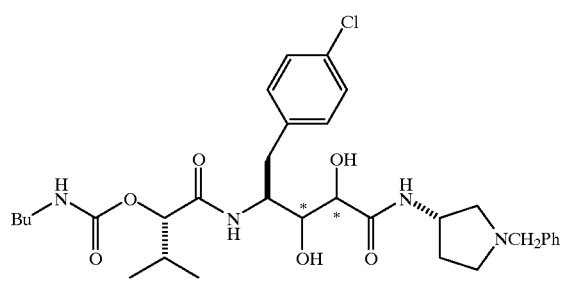
9 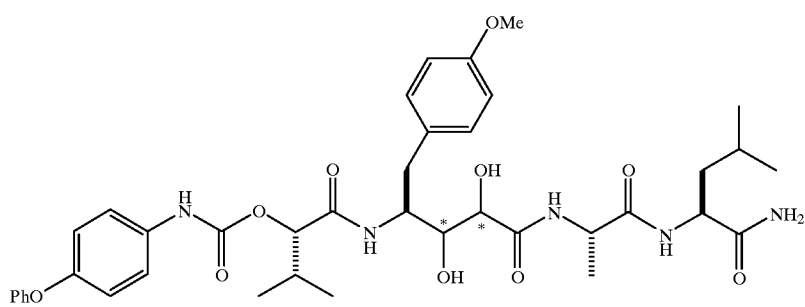
10 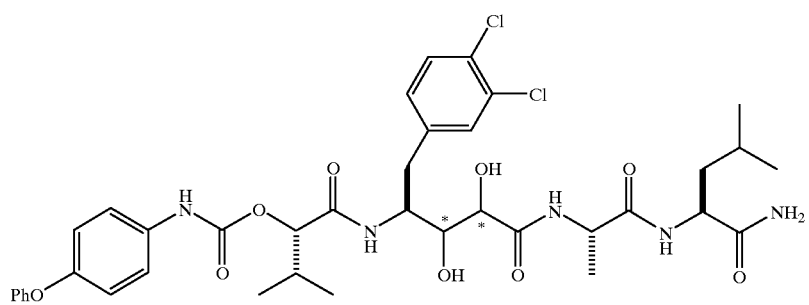
11 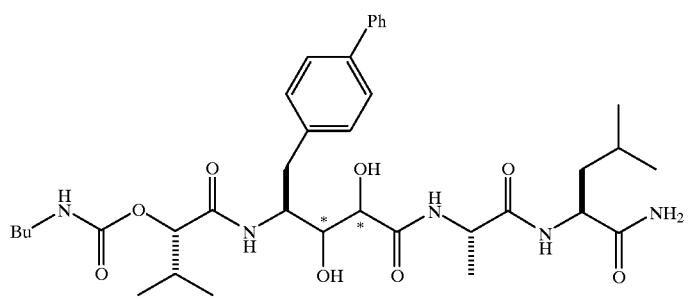

TABLE 2-continued
12
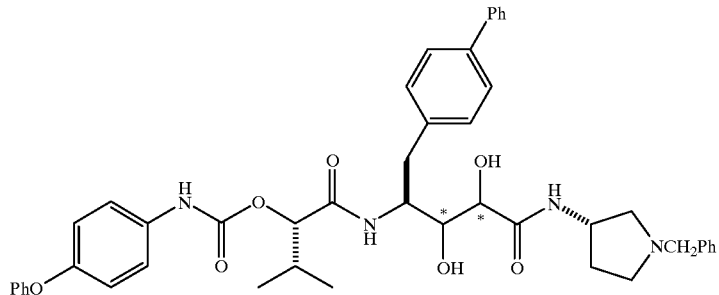
13
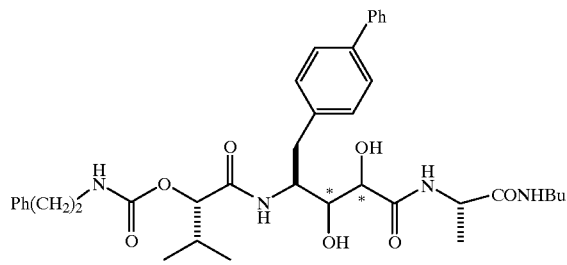
14
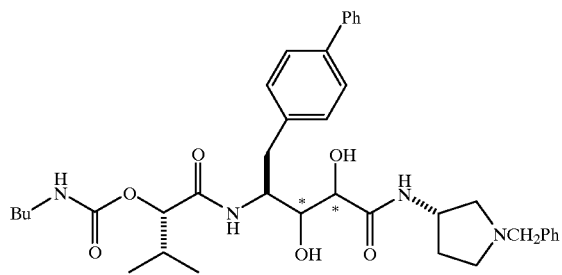
15
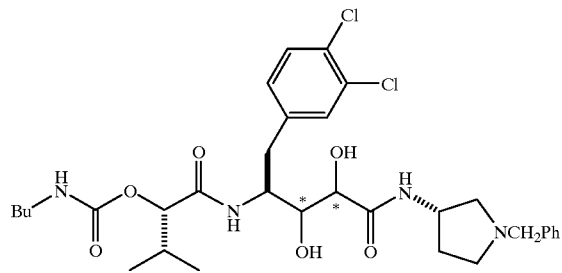
16
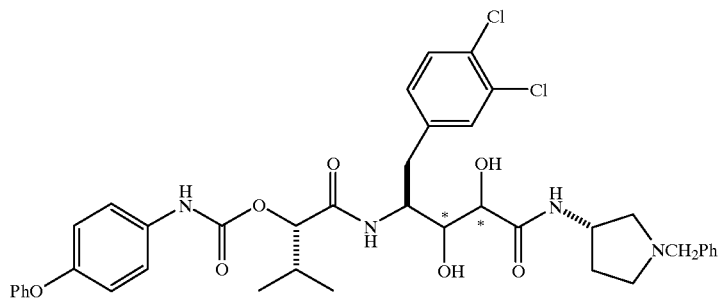

TABLE 2-continued
17 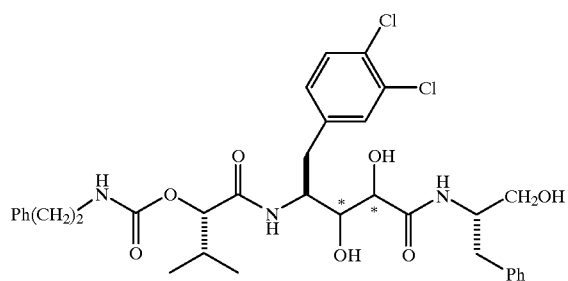
18 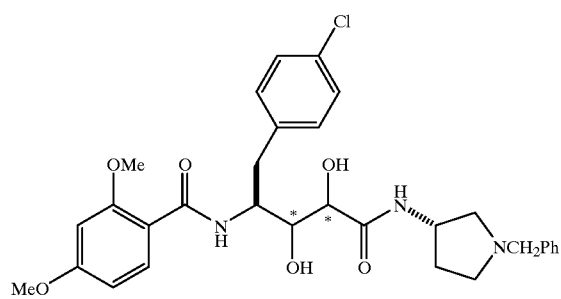
19 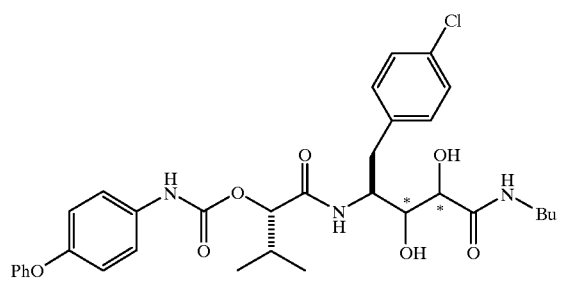
20 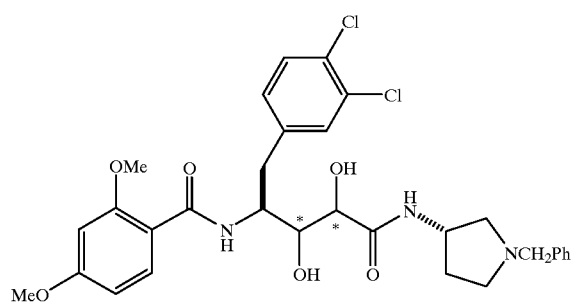
21 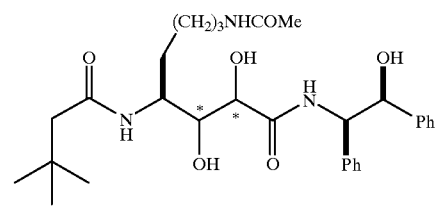

TABLE 2-continued
22
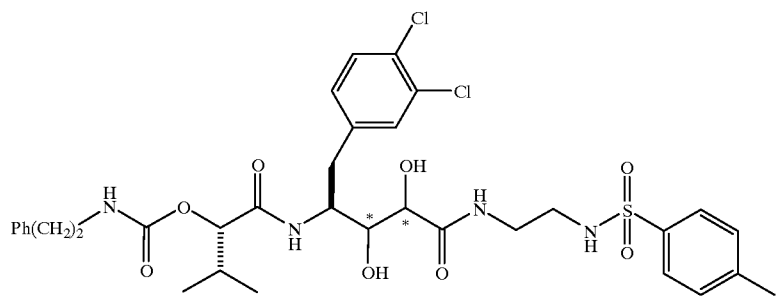
23
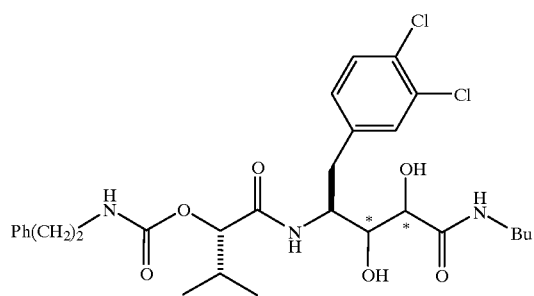
24
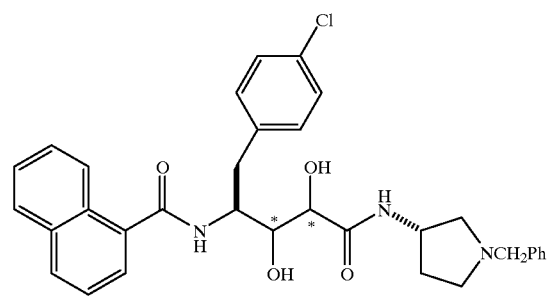
25
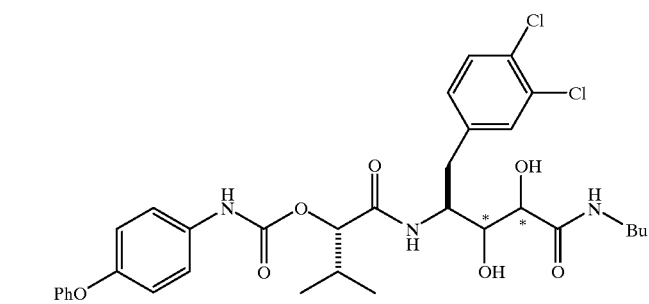
26
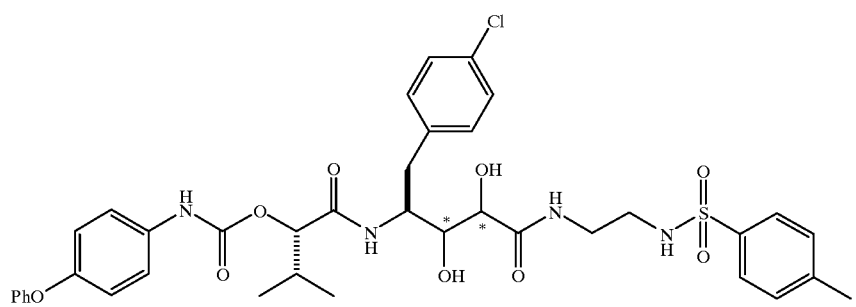

TABLE 2-continued
27 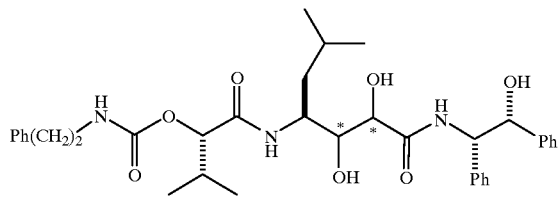
28 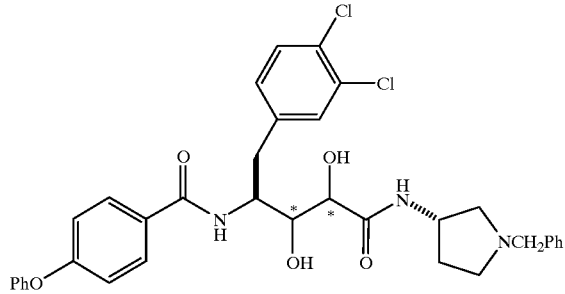
29 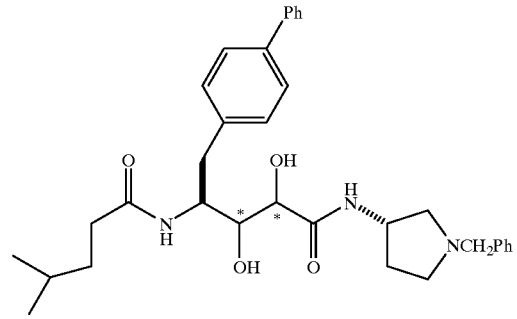
30 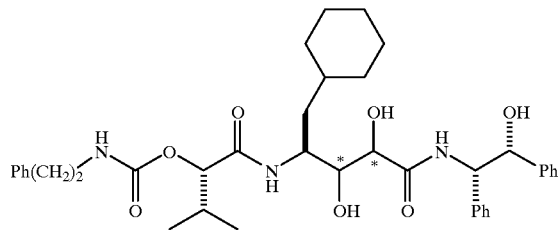
31 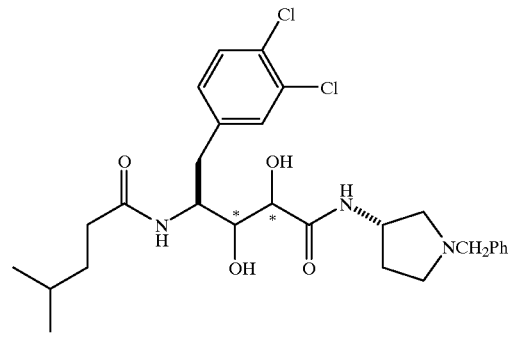

TABLE 2-continued
| Entry | Structure |
|---|---|
| 32 | 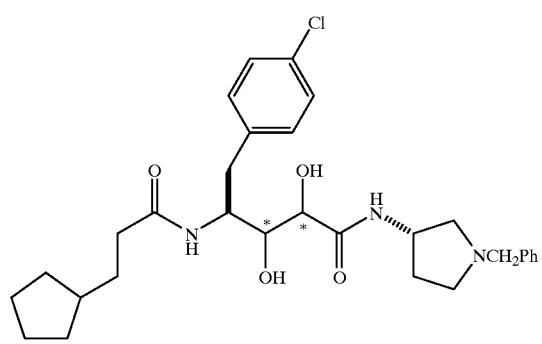 |
| 33 | 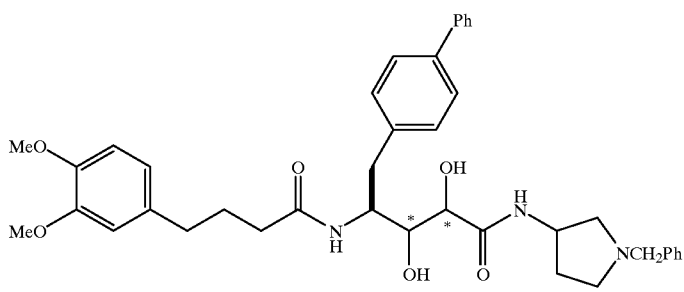 |
| 34 | 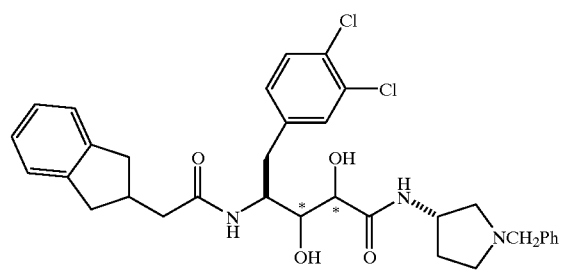 |
Hydroxystatine amides - Cathepsin D Inhibitors
| Entry | Structure |
|---|---|
| 35 | 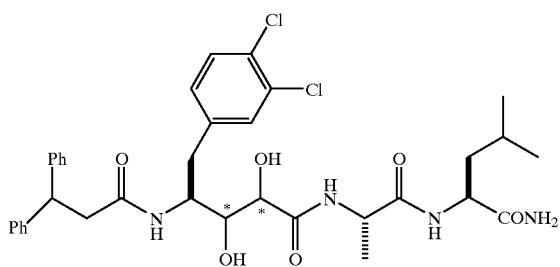 |
| 36 | 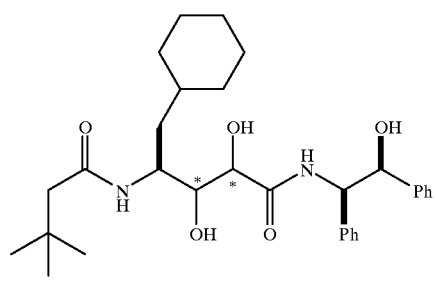 |

TABLE 2-continued
37
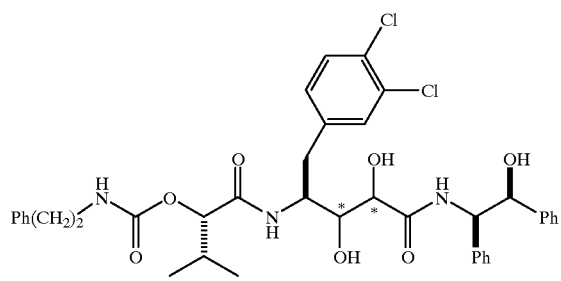
38
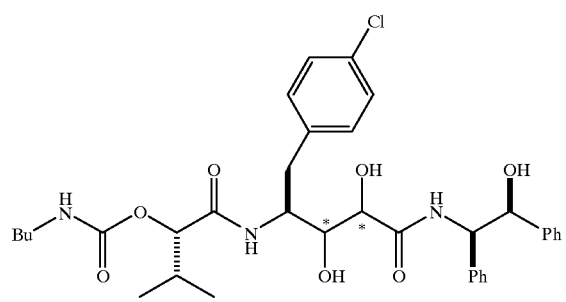
39
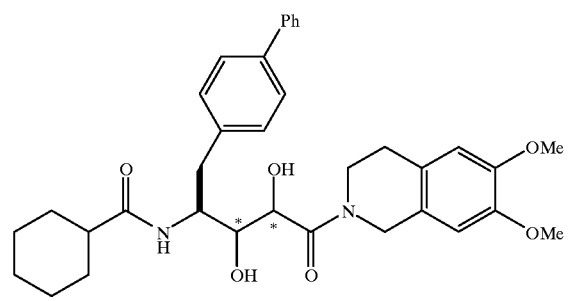
40
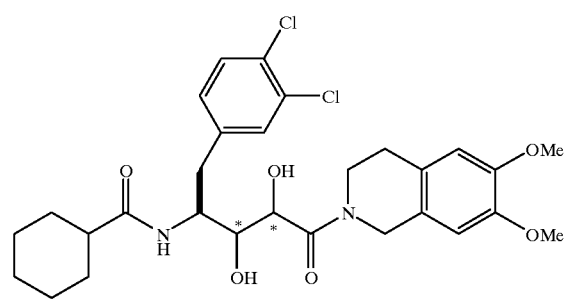
41
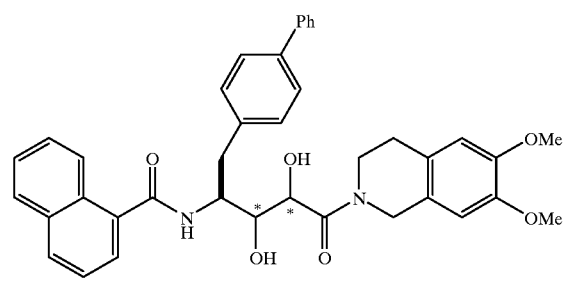

TABLE 2-continued

42
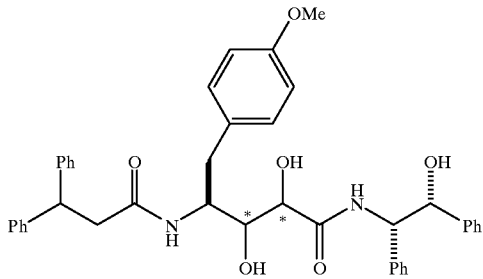

43
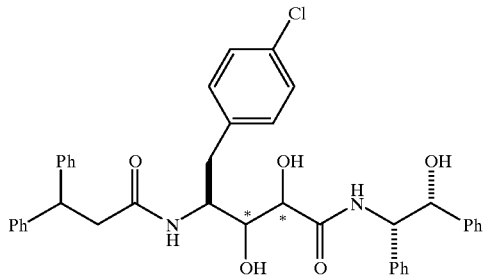

44
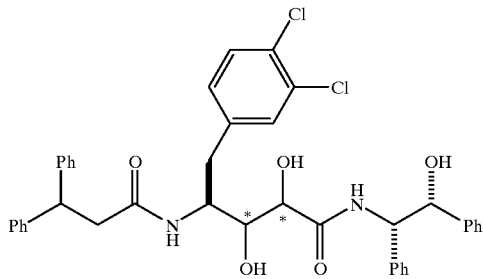

45
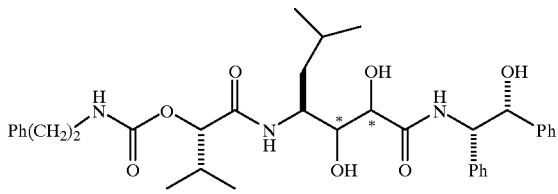

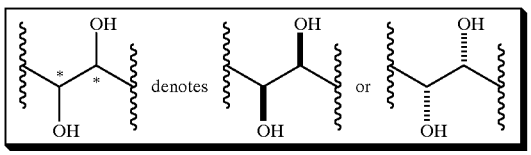

VI. Pharmaceutical Compositions—Administration

Any suitable route of administration may be employed for providing a patient with an effective dosage of compounds of the invention. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise the inventive hydroxystatine amides and hydroxyphosphonates as the active ingredients, and may also contain a pharmaceutically acceptable carrier, and optionally, other therapeutic ingredients. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. Methods for their preparation are well known in the art.

Because of their ease of administration, tablets and capsules represent the most advantageous oral dosage unit forms, in which case solid pharmaceutical carriers are employed. If desired, tablets may be coated by standard aqueous or nonaqueous techniques. In addition to the common dosage forms set out above, the compounds of the present invention may also be administered by controlled or sustained release means and delivery devices.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods or pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

We claim:

1. A compound of Formula I

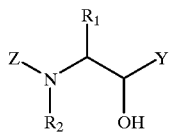

wherein:
- $R^1$ is chosen from the group consisting of alkyl, —(CH$_2$)$_n$-cycloalkyl, —(CH$_2$CH$_2$)$_n$NHC(O)-alkyl, and arylalkyl, wherein n=1–3;
- $R^2$ is H or ⓢ—C(O)—L—, wherein ⓢ is a solid support, and —L— is a linker;
- $R^7$ is H, alkyl, arylalkyl, or —(CH$_2$)$_n$-cycloalkyl; and
- $R^8$ is alkyl, arylalkyl, or aryl.

2. The compound of claim 1 wherein:
$R^2$ is H.

3. The compound of claim 1 wherein:
$R^2$ is ⓢ—C(O)—L—, wherein ⓢ is a solid support, and —L— is a linker.

4. The compound of claim 3 wherein:

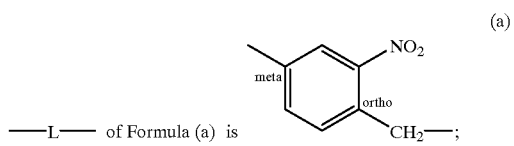

wherein the designated meta-position is attached to the —C(O)— and the ortho-methylene attaches to the amide nitrogen of Formula I.

5. The compound of claim 2 wherein:
Y is —P(O)(OR$^3$)$_2$, wherein R$^3$ is arylalkyl or haloalkyl; and
Z is —C(O)C(H)(R$^7$)OC(O)NHR$^8$, wherein R$^7$ is H, alkyl, arylalkyl, or —(CH$_2$)$_n$-cycloalkyl, and R$^8$ is alkyl, arylalkyl, or aryl.

6. A method for conducting antimalarial therapy in a human suffering from malaria, comprising administering to said human a therapeutically effective amount of a compound of claim 2 or 5.

7. A method for treating Alzheimer's disease in a human, which comprises administering to said human a therapeutically effective amount of a compound of claim 2 or 5.

* * * * *

UNITED STATES PATENT AND TRADEMARK OFFICE
CERTIFICATE OF CORRECTION

PATENT NO. : 6,150,344
DATED : November 21, 2000
INVENTOR(S) : Carroll et al.

It is certified that error appears in the above-identified patent and that said Letters Patent are hereby corrected as shown below:

IN THE CLAIMS:

Claim 1, Col. 39, line 36, after "linker;", insert

--Y is -P(O)(OR$^3$)$_2$, wherein R$^3$ is alkyl, arylalkyl, or haloalkyl; and

Z is -C(O)C(H)(R$^7$)OC(O)NHR$^8$, wherein--.

Signed and Sealed this

Eighth Day of May, 2001

Attest:

NICHOLAS P. GODICI

*Attesting Officer*    *Acting Director of the United States Patent and Trademark Office*